(12) United States Patent
Peschel et al.

(10) Patent No.: US 6,696,610 B2
(45) Date of Patent: Feb. 24, 2004

(54) CONTINUOUS PREPARATION OF MONOETHANOLAMINE, DIETHANOLAMINE AND TRIETHANOLAMINE

(75) Inventors: Werner Peschel, Freinsheim (DE); Axel Hildebrandt, Neustadt (DE); Bernd Bessling, Grünstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/227,831

(22) Filed: Aug. 27, 2002

(65) Prior Publication Data

US 2003/0065224 A1 Apr. 3, 2003

(30) Foreign Application Priority Data

Sep. 5, 2001 (DE) .......................... 101 43 424

(51) Int. Cl.$^7$ .......................... C07C 213/04; B01D 3/34
(52) U.S. Cl. ...................... 564/463; 564/477
(58) Field of Search ................. 564/475, 472

(56) References Cited

U.S. PATENT DOCUMENTS

| | | | | |
|---|---|---|---|---|
| 1,904,013 A | * | 4/1933 | Reid et al. ................. | 564/477 |
| 2,823,236 A | * | 2/1958 | Lowe et al. ................. | 564/477 |
| 3,585,239 A | * | 6/1971 | Stein et al. ................. | 564/477 |
| 4,355,181 A | * | 10/1982 | Willis, Jr. et al. ........... | 564/477 |
| 4,847,418 A | * | 7/1989 | Gibson et al. .............. | 564/477 |
| 6,075,168 A | * | 6/2000 | DiGuilio et al. ............ | 564/487 |

OTHER PUBLICATIONS

Derwent Abst J 7 7002–887, 1968.

\* cited by examiner

*Primary Examiner*—Brian Davis
(74) *Attorney, Agent, or Firm*—Keil & Weinkauf

(57) ABSTRACT

A continuous process for the preparation of monoethanolamine, diethanolamine and triethanolamine by reacting ammonia and ethylene oxide in liquid phase in the presence of water as catalyst in a pressure column is proposed, where, as a result of the heat of the reaction, some of the ammonia evaporates, condenses at the head of the column and is again charged to the column, the reaction mixture at the bottom end of the pressure column is drawn off and then separated, the pressure column is constructed as a reactive distillation column (I) with evaporator at the bottom (S) and where, by means of inputting energy via the evaporator at the bottom (S), the weight ratio of monoethanolamine to diethanolamine to triethanolamine is controlled and, via the ratio of ammonia to ethylene oxide in the feed to the reactive distillation column (I), the ammonia proportion in the bottom product from the reactive distillation column (I) is controlled.

15 Claims, 4 Drawing Sheets

CONTINUOUS PREPARATION OF MONOETHANOLAMINE, DIETHANOLAMINE AND TRIETHANOLAMINE

The invention relates to a continuous process for the preparation of monoethanolamine, diethanolamine and triethanolamine by reacting ammonia in ethylene oxide with liquid phase in the presence of water.

On an industrial scale, ammonia is reacted with ethylene oxide in the presence of water as catalyst to prepare the ethanolamines monoethanolamine, diethanolamine and triethanolamine, referred to below in abbreviated form as MEA, DEA and TEA, respectively, by irreversible reactions according to the following equations $$NH_3 + C_2H_4O \rightarrow NH_2C_2H_4OH$$

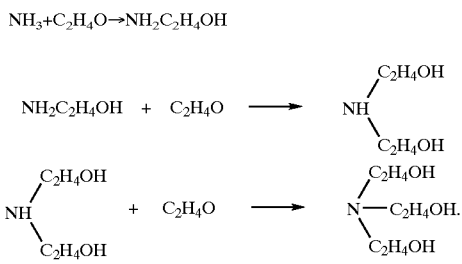

Usually, a particularly high proportion of MEA is desired, as is one of DEA, whereas TEA should usually represent the smallest possible proportion of the ethanolamine mixture obtained since there is another more economical preparation route for this. Since the consecutive reactions to DEA and/or TEA each have rate constants which exceed those of the reaction to give MEA by in each case about 10 times, a high ammonia to ethylene oxide ratio in the reaction zone is a prerequisite for a high proportion of MEA in the product mixture of the ethanolamines. A high excess of ammonia, however, has the disadvantage, where it is also retained in the product mixture, that it has to be recovered again, which involves extra expenditure.

According to a known process, a continuously operated tubular reactor is used for the production of ethanolamines. In order to obtain a proportion by weight of MEA in the product mixture of the ethanolamines of 60% by weight, a molar feed ratio of ammonia to ethylene oxide in the reactor feed of 10:1 must be used. To separate the product mixture, at least one distillation column is required to separate off ammonia and a further distillation column is required to separate off water, in each case as overhead take-off. The ammonia/water mixture which forms in high excess, corresponding approximately to three times the product mixture of the ethanolamines, in each case in mass flows, is returned to the tubular reactor. In order to set the monoethanolamine proportion in the resulting ethanolamine mixture to a value in the frequently desired range between 35 and 80% by weight, it would be necessary in this procedure to vary the molar feed ratio of ammonia to ethylene oxide in the range between 5:1 and 30:1. This would require a high flexibility in the ammonia separation, which can only be achieved with high technical complexity.

Japanese laid-open specification JP 2887/77 discloses a process for the preparation of ethanolamines by reacting ammonia with ethylene oxide in the presence of water, a significantly higher ammonia to ethylene oxide ratio in the reaction zone compared with the reactor feed and thus an increased proportion of monoethanolamine in the product mixture of the ethanolamines being achieved by providing gas-liquid contact surfaces (evaporation surfaces) in the reactor, on which the ammonia evaporates as a result of the heat of the reaction, then condenses and the condensate is returned to the reaction zone. The temperature and thus the pressure in the reactor is regulated by the amount of evaporated ammonia. The ammonia:ethylene oxide molar ratio in the reactor feed is, for example, 3.5:1. The reactor is regulated by maintaining the ammonia content at the reactor outlet, based on the ethanolamines, to 30 mol % or more.

The process thus permits an increased proportion of the especially desired MEA in the product mixture of the ethanolamines with a simultaneously lower ammonia excess in the ammonia/ethylene oxide feed stream compared with the known process in the tubular reactor, by utilizing the heat of the reaction for evaporating ammonia. The available heat of the reaction, however, at the same time limits the scope with regard to MEA to DEA to TEA ratio in the product mixture of the ethanolamines. In order to obtain higher proportions of MEA in the product mixture, it is necessary to use an increased ammonia excess in the feed stream, with the disadvantage that the reactor discharge has a relatively high proportion of ammonia and thus the work-up of the reactor discharge with recovery of the ammonia is complex, in particular is not possible in a single atmospheric-pressure column whose head condenser can be cooled with river water. The weight ratio of MEA to DEA to TEA in the product mixture can thus not be regulated as desired.

It is an object of the present invention to provide a process for the preparation of MEA, DEA and TEA which is more economical, in particular requires lower investment costs, and which is more flexible, in particular ensures a change in the relative concentrations of the ethanolamines in the product mixture as required, and where the product discharge can always be adjusted so that the purification of ethanolamine by distillation and ammonia/water recovery are possible in a single distillation column with a cost-effective configuration, i.e. in particular at atmospheric pressure and using river water for the condensation.

We have found that this object is achieved by a continuous process for the preparation of monoethanolamine, diethanolamine and triethanolamine by reacting ammonia with ethylene oxide in the liquid phase in the presence of water as catalyst in a pressure column, where, as a result of the heat of the reaction, some of the ammonia evaporates, condenses at the head of the column and is again charged to the column, the reaction mixture is drawn off at the lower end of the pressure column and is then separated.

The invention involves the pressure column being constructed as a reactive distillation column with evaporator at the bottom and, by means of the input of energy via the evaporator at the bottom, regulating the weight ratio of monoethanolamine to diethanolamine to triethanolamine and, via the ratio of ammonia to ethylene oxide in the feed to the reactive distillation column, regulating the ammonia proportion in the bottom product from the reactive distillation column.

It has been found that, despite the safety problems in the handling of ethylene oxide, the reaction of ammonia with ethylene oxide can be carried out in a reactive distillation column and in this connection, by means of inputting energy via the evaporator at the bottom of the reactive distillation column, it is possible to control the ratio of ethanolamines to one another, it being possible to simultaneously regulate the ammonia content in the bottom product via the ratio of ammonia to ethylene oxide with the feed to the reactive distillation column always in such a way that the separation of the bottom product into the ethanolamines and into ammonia-water is possible in a cost-effective manner in a single distillation column.

With regard to the reactive distillation columns which can be used, there are in principle no limitations; suitable columns are all those in which a chemical reaction and separation by distillation or rectification can be carried out.

The reactive distillation column preferably contains plates as separation-effecting internals; plate columns have the advantage that a sufficiently high hold-up is available for the reaction of ammonia with ethylene oxide.

A feed stream of ammonia and ethylene oxide, preferably in vapor form, is fed to the reactive distillation column, in the upper part thereof, preferably above the uppermost column plate. For a reactive distillation column operating under ideal conditions, the stoichiometric ratio of ammonia to ethylene oxide in the feed stream is to be adjusted to correspond to the desired MEA to DEA to TEA ratio in the product mixture. However, in order to ensure that the highly explosive ethylene oxide does not bleed through into the bottom of the column, ammonia is preferably introduced in a slightly stoichiometric excess, i.e. with a molar ratio toward ethylene oxide in the range from 3:1 to 1.01:1, particularly preferably with a molar ratio of about 1.3:1. The slight excess of ammonia ensures that ethylene oxide is completely reacted.

The stream of vapors from the reactive distillation column is condensed in a condenser at the head of the column or outside of the reactive distillation column and is again charged in its entirety to the column. There is thus no take-off of low boiling components at the head of the column. Only noncondensable fractions of the vapor stream which may sometimes arise are drawn off.

An evaporator at the bottom is arranged at the bottom of the column, via which heat energy is introduced into the reactive distillation column.

According to the invention, regulating the input of energy via the evaporator at the bottom, the ratio of the ethanolamines to one another is controlled and, via the ratio of ammonia to ethylene oxide in the feed to the reactive distillation column, the ammonia proportion in the bottom product from the reactive distillation column is controlled.

The ammonia proportion in the bottom product from the reactive distillation column is preferably regulated so that the bottom product from the reactive distillation column can be separated into ammonia and water on the one hand and into the ethanolamines on the other hand in a single distillation column at atmospheric pressure, with condenser at the head of the column, using river water as cooling medium. It has been found that the ammonia proportion in the bottom product of the reactive distillation column is decisive for the economic feasibility of the overall process and that it is possible to observe an upper limit for the ammonia proportion in the bottom product, making it possible to separate the bottom product in a single atmospheric-pressure column, with river water cooling at the head of the column.

To do this, the ammonia proportion in the bottom product from the reactive distillation column should particularly preferably be at most 10% by weight, preferably at most 5% by weight, particularly preferably at most 2% by weight. It has hitherto been assumed that a higher proportion of ammonia in the bottom product is required in order to ensure a sufficiently high ammonia proportion in the reaction mixture for the reaction to give the preferred higher monoethanolamine proportions in the product mixture.

In a preferred process variant, the reactive distillation column is designed so that, below the reaction zone, which occupies the majority of the column, a reaction-free zone is attached in which the reaction mixture can be further depleted of ammonia.

It has been found that the MEA concentration in % by weight, based on the total weight of MEA, DEA and TEA for a given number of theoretical plates can be regulated by the input of energy to the evaporator at the bottom, based on the total weight of MEA, DEA and TEA, corresponding to the diagram in FIG. 1. The diagram shows that as the input of energy increases, the MEA concentration increases steeply at first, and then gradually more gently.

The reactive distillation column is a pressure column. It is preferably operated at a column pressure in the range from 10 to 80 bar absolute, preferably 40 bar absolute. As a result of the upper limit of the pressure range for a given ammonia proportion in the bottom product, the temperature at the bottom is correspondingly limited, and as a result it is ensured that no or only small proportions of color-imparting and thus specification-harmful secondary components arise. The bottom temperature at the bottom for this should not exceed 185° C., preferably 183° C., particularly preferably 180° C.

It has been found that the reactive distillation column is preferably designed so that the number of theoretical plates is determined as a function of the input of energy into the still, for a given MEA concentration, in accordance with the diagram in FIG. 2. The curve in FIG. 2 shows that, with an increasing number of plates, the required input of energy decreases rapidly at first, and then ever more slowly.

According to a preferred process variant, from the separation column for ammonia and water on the one hand and MEA, DEA and TEA on the other hand, the ammonia- and water-containing head product is returned, preferably in its entirety, via a condenser at the head of the reactive distillation column to the head region thereof. By recycling the overhead stream of the distillation column, the economic feasibility of the overall process is improved.

Some of the energy input into the bottom evaporator at the bottom can preferably be replaced by the input of side energy. As a result, it is possible to use, in a cost-effective manner, at least partially, a vapor with a lower pressure and thus lower costs.

It is preferably also possible to draw off the reaction mixture or part of the reaction mixture from the upper region of the reactive distillation column, in particular from a position between the 1st and 15th theoretical plate, particularly preferably from the 1st theoretical plate, to pass it into one or more residence-time vessels, for example one or more tubular reactors and, after a reaction has taken place, to return it from the residence-time vessel(s) again to the reactive distillation column below the take-off from same, preferably one plate below the take-off from the reactive distillation column.

The invention is illustrated in more detail below by reference to a drawing and a working example.

Specifically:

The theoretical plates are in this case counted from head to bottom in the reaction distillation column I.

Figure 1:
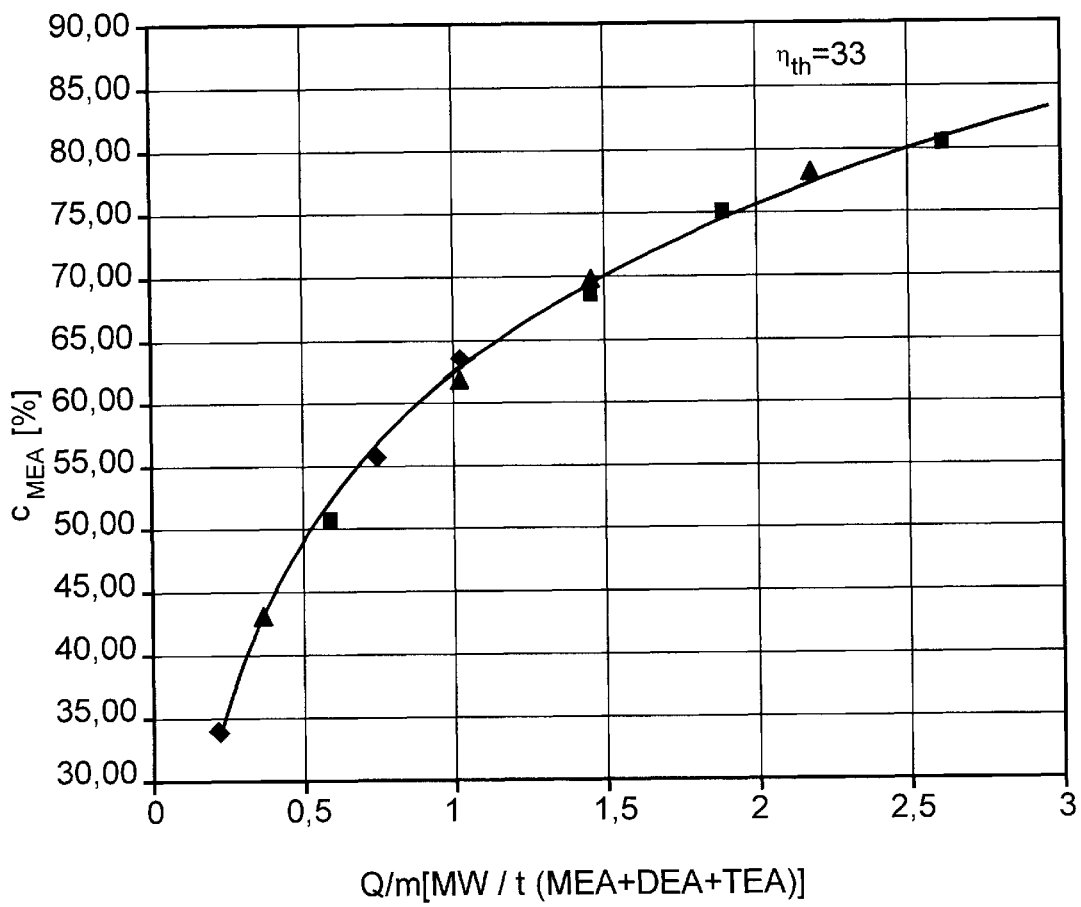
FIG. 1 shows a diagram of the MEA concentration, based on the total weight of MEA, DEA and TEA in % by weight ($C_{MEA}$ [%]) as a function of the energy input Q to the evaporator at the bottom per total weight m of MEA, DEA and TEA Q/m[MW/t(MEA+DEA+TEA] for a given number of theoretical plates $n_{th}$ where MW is the unit megawatt and t is the unit tonne, FIG. 2 shows a diagram of the theoretical number of plates $n_{th}$ as a function of the energy input Q to the bottom evaporator at the bottom per tonne of the total weight of MEA, DEA and TEA Q/m[MW/t(MEA+DEA+TEA], for a given MEA concentration ($C_{MEA}$ [%]), FIG. 3 shows a process scheme for a preferred embodiment of the process according to the invention and FIG. 4 shows profiles of the reactive distillation column from the variant shown in FIG. 3, FIG. 4a as a function of temperature, T FIG. 4b as a function of the mole percentages (mol %) in the liquid phase and FIG. 4c as a function of the reaction rates (v) in kmol per hour (kmol/h), in each case based on the theoretical plates $n_{th}$.

The curve in FIG. 1 shows that the MEA concentration in % by weight ($C_{MEA}$[%]) increases steeply at first and then increases gradually more gently with increasing input of energy via the evaporator at the bottom, based on the total weight of MEA, DEA and TEA Q/m[MW/t(MEA+DEA+TEA)].

Figure 2:
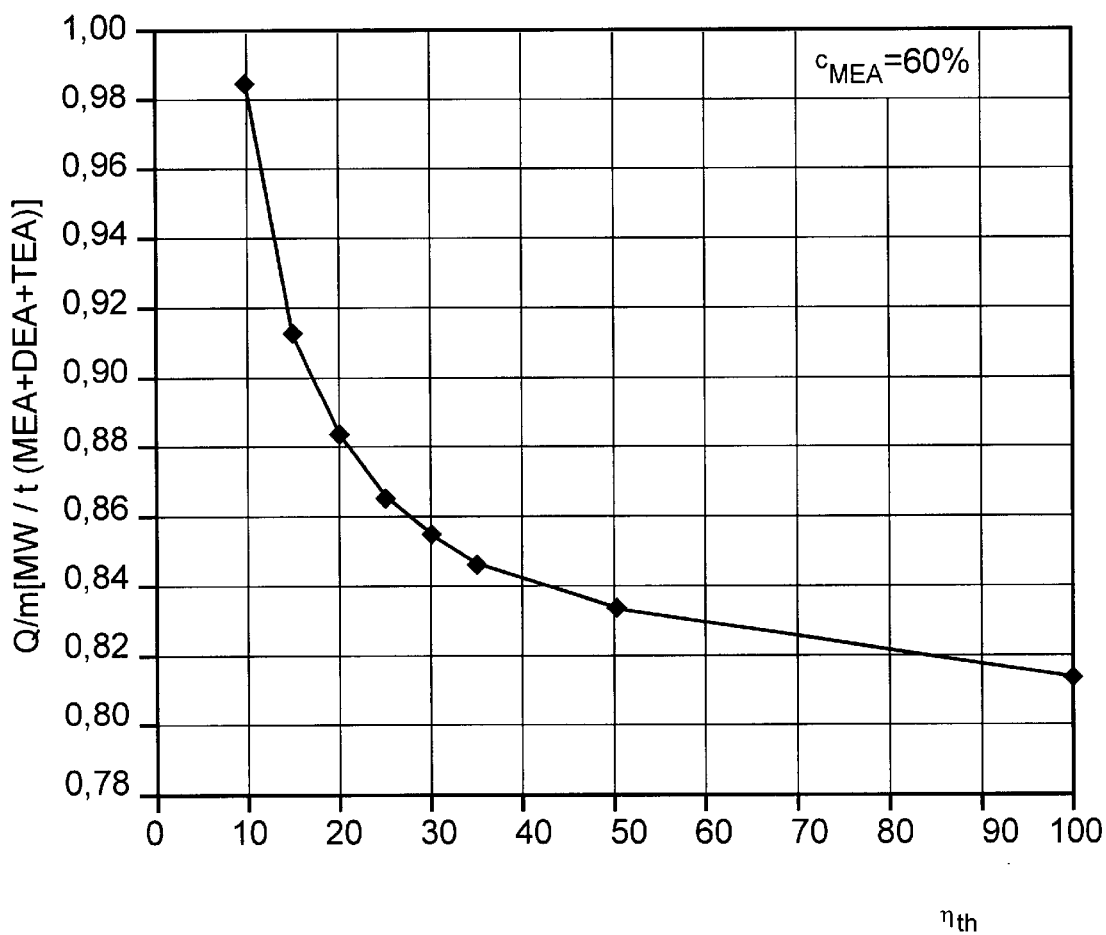

The curve in FIG. 2 shows that the energy input Q/m [MW/t(MEA+DEA+TEA] decreases at first rapidly and then more slowly with an increasing number of theoretical plates $n_{th}$, for a given MEA concentration ($C_{MEA}$[%]).

Figure 3:
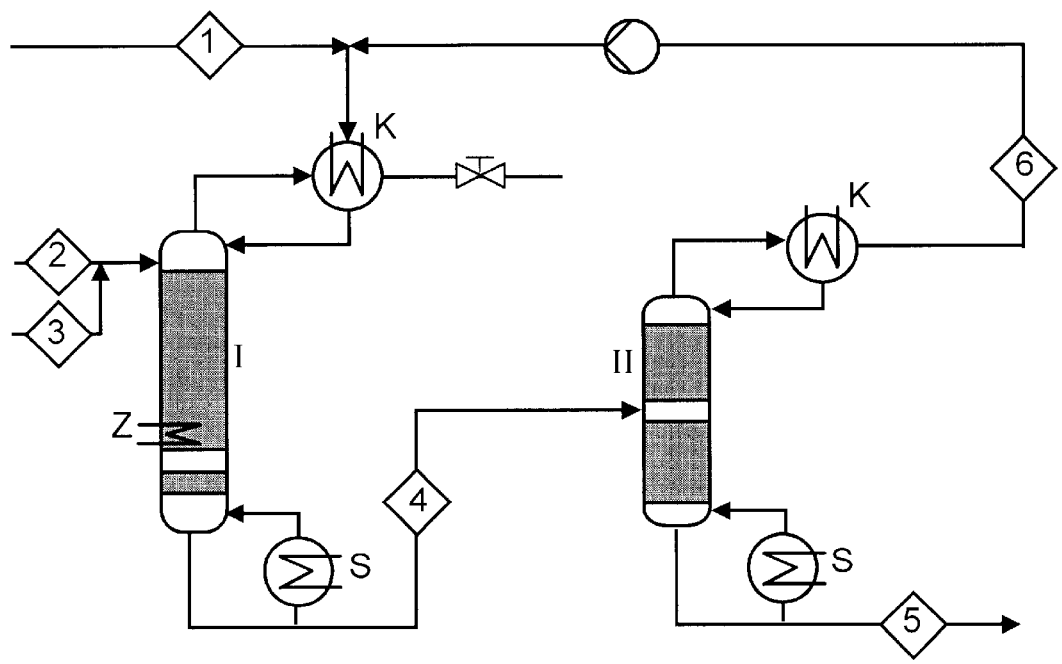

The process scheme in FIG. 3 of a preferred embodiment shows a reactive distillation column I with supply of a feed stream of ammonia and ethylene oxide in the upper region thereof, condenser K at the head of the column, evaporator at the bottom S and intermediate evaporator Z. The bottom product from the reactive distillation column I is passed to a distillation column II, in the middle region thereof, the vapor stream of which is condensed in a condenser K at the head of the distillation column II and is then recycled to the reactive distillation column I. The distillation column II is likewise equipped with a evaporator at the bottom S. The bottom product from the distillation column II comprises the ethanolamines MEA, DEA and TEA. The reference numerals 1 to 6 refer to the stream: 1 is the water top-up stream, 2 is the feed stream of ethylene oxide, 3 is the top-up stream of ammonia, 4 is the bottom product from the reactive distillation column I, 5 is the bottom product from distillation column II and 6 is the recycle stream from the head of the distillation column II to the head of the reactive distillation column I.

Figure 4A:
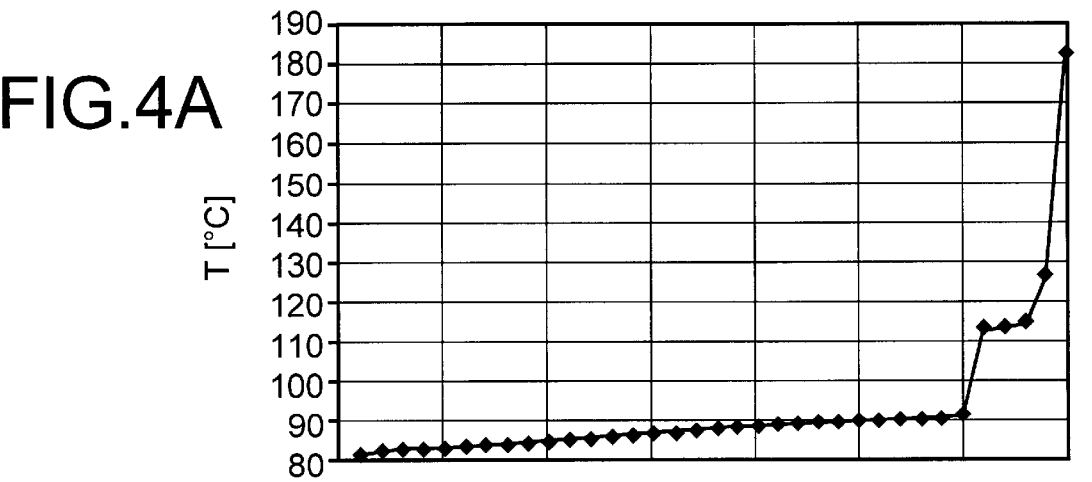
Figure 4B:
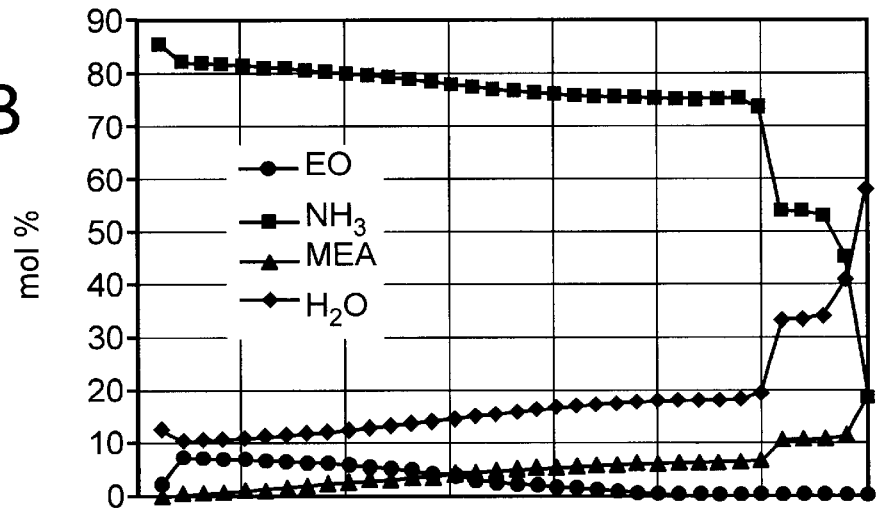
Figure 4C:
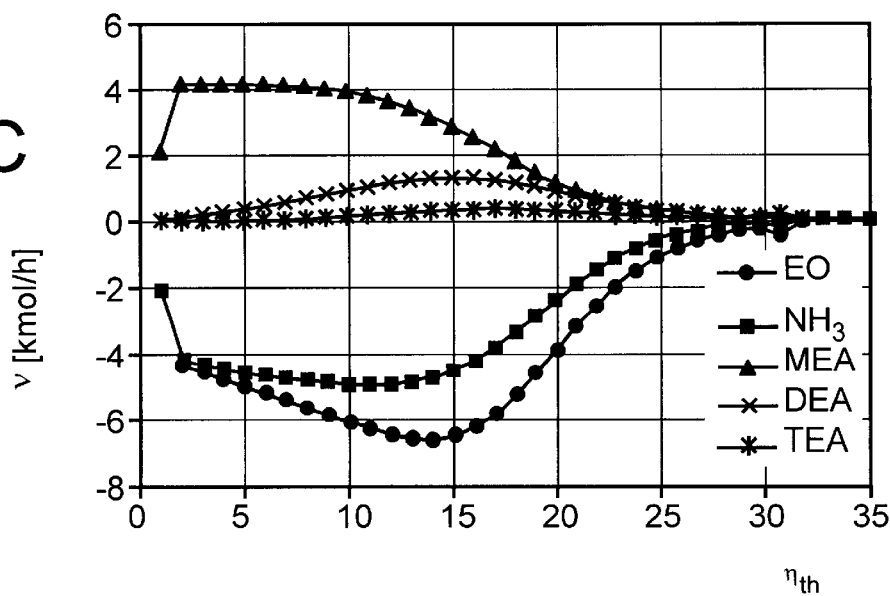

FIG. 4 shows the profiles in the reactive distillation column I, FIG. 4a showing the temperature T [° C.], FIG. 4b showing the mole percentages of the components in the liquid phase and FIG. 4c showing the reaction rates in kmol per hour v [kmol/h], in each case as a function of the theoretical plates $n_{th}$.

FIG. 4a shows that the temperature in the reactive distillation column increases gradually to theoretical plate 30, up to about 90° C., and then increases suddenly, to about 181° C., in the bottom of the column.

FIG. 4b shows that the ethylene oxide concentration decreases with increasing plate number, and that from plate 25, ethylene oxide is virtually no longer present in the liquid phase. The ammonia concentration decreases gradually to plate 30, and then decreases suddenly to the lowest plates of the reactive distillation column.

FIG. 4c shows the reaction rates with regard to ethylene oxide (EO), ammonia, and the ethanolamines MEA, DEA and TEA as a function of the theoretical plate $n_{th}$. The conversions spread out over all theoretical plates from the head of the column to the 30th theoretical plate. In each case they achieve a relative maximum between the 10th and the 17th theoretical plate.

EXAMPLE 1

In a plant as shown diagrammatically in FIG. 3, with a reactive distillation column I of height 32 m and a column diameter of 1.5 m, a column hold-up of 20 m³ and a number of 30 reactive theoretical plates, and of an additional 3 theoretical plates in the lower, reaction-free region of the reactive distillation column I, with a head pressure of 35 bar, a temperature at the head of the column of 80° C. and a temperature at the bottom of 181 ° C., a continuous procedure, taking as a basis a feed stream 2 of 5321 kg/h of ethylene oxide, 2776 kg/h of ammonia, corresponding to an ammonia/ethylene oxide molar ratio of 1.3:1 and 4000 kg/h of water, with an energy input of 2500 kilowatts via the evaporator at the bottom and of 3250 kilowatt via an intermediate evaporator at the 31st plate gave a bottom product (stream 4) containing 9.8% by weight of ammonia. This corresponds to a total energy input of 5.57 MW. Supplying the same to the middle region of a distillation column II with a height of 19 m, a diameter of 1.4 m and 16 theoretical plates, a column pressure of 1.1 bar at a temperature at the head of the column of 41° C. and a temperature at the bottom of 182° C. gave an overhead stream 6 with complete recycling to the reactive distillation column I, and a bottom stream 5, comprising the ethanolamines MEA, DEA and TEA. The composition of streams 1 to 6 in % by weight, and in each case the total amount thereof in kg/h are given in table 1 below:

TABLE 1

| Stream No. | 1 | 2 | 3 | 4 | 5 | 6 |
|---|---|---|---|---|---|---|
| Proportion by weight [%] | | | | | | |
| H₂O | 100.0 | | | 33.2 | 0.2 | 77.1 |
| NH₃ | | | 100.0 | 9.8 | | 22.9 |
| EO | | 100.0 | | | | |
| MEA | | | | 34.5 | 60.4 | 500 ppm |
| DEA | | | | 16.9 | 29.6 | |
| TEA | | | | 5.6 | 9.8 | |
| Total amount kg/h | 10 | 5321 | 1573 | 12083 | 6904 | 5179 |

EXAMPLE 2

With the same plant and the same process parameters, but with a lower input of energy of only 3450 kW, streams 1 to 6, which have the same meaning as in example 1, were obtained, but with the compositions given in table 2 below:

| Stream-No. | 1 | 2 | 3 | 4 | 5 | 6 |
|---|---|---|---|---|---|---|
| Proportion by weight [%] | | | | | | |
| H₂O | 100.0 | | | 33.2 | 0.2 | 77.2 |
| NH₃ | | | 100.0 | 9.8 | | 22.8 |
| EO | | 100.0 | | | | |
| MEA | | | | 28.5 | 49.9 | 500 ppm |
| DEA | | | | 18.9 | 33.1 | |
| TEA | | | | 9.6 | 16.8 | |
| Total amount kg/h | 10 | 5430 | 1464 | 12083 | 6904 | 5179 |

Thus, varying the energy input Q/m[MW/t(MEA+DEA+TEA] from about 0.83 in example 1 to about 0.5 in example 2 results in a change in the MEA content, based on the total weight of the ethanolamines MEA+DEA+TEA ($C_{MEA}$ [%]) from 60 in example 1 to 50 in example 2.

In both examples, the ammonia proportion in stream 4 was 9.8% by weight and could be separated off from the ethanolamines in a single distillation column.

We claim:

1. A continuous process for the preparation of monoethanolamine, diethanolamine and triethanolamine by reacting ammonia and ethylene oxide in liquid phase in the presence of water as catalyst in a pressure column, where, as a result of the heat of the reaction, some of the ammonia evaporates, condenses at the head of the column and is again charged to the column, the reaction mixture is drawn off at the lower end of the pressure column and is then separated, wherein the pressure column is constructed as a reactive distillation column with evaporator at the bottom and where, by means of inputting energy into the evaporator at the bottom, the weight ratio of monoethanolamine to diethanolamine to triethanolamine is controlled and, via the ratio of ammonia to ethylene oxide in the feed to the reactive distillation column, the ammonia proportion in the bottom product from the reactive distillation column is controlled such that the bottom product from the reactive distillation column can be separated into ammonia and water on the one hand and into monoethanolamine, diethanolamine and triethanolamine on the other hand in a single distillation column.

2. A process as claimed in claim 1, wherein the feed stream of ammonia and ethylene oxide, having a molar ratio of ammonia to ethylene oxide in the range from 3:1 to 1.01:1, is passed to the reactive distillation column in the upper region thereof.

3. A process as claimed in claim 1, wherein the ammonia proportion in the bottom product from the reactive distillation column is regulated such that the sole distillation column in which the bottom product from the reactive distillation column is separated operates at atmospheric pressure with a condenser at the head of the column using river water as cooling medium.

4. A process as claimed in claim 3, wherein the ammonia proportion in the bottom product of the reactive distillation column is at most 10% by weight, based on the total weight of the bottom product.

5. A process as claimed in claim 1, wherein the reactive distillation column has, below a reaction zone which occupies the majority of the column, a reaction-free zone in which the reaction mixture is further depleted of ammonia.

6. A process as claimed in claim 1, wherein the monoethanolamine concentration, based on the total weight of monoethanolamine, diethanolamine and triethanolamine, for a given number of theoretical plates, is regulated via the input of energy to the evaporator at the bottom based on the total weight of monoethanolamine, diethanolamine and triethanolamine.

7. A process as claimed in claim 1, wherein the reactive distillation column is operated at a column pressure of from 10 to 80 bar absolute.

8. A process as claimed in claim 1, wherein, from the distillation column, to separate ammonia and water on the one hand monoethanolamine, diethanolamine and triethanolamine on the other hand, the ammonia- and water-containing head product is returned via a condenser on the head of the reactive distillation column, to the head region thereof.

9. A process as claimed in claim 1, wherein some of the input of energy to the evaporator at the bottom is replaced by the input of energy supplied by an intermediate reboiler.

10. A process as claimed in claim 1, wherein the feed stream of ammonia and ethylene oxide is passed to the reactive distillation column in vapor form.

11. A process as claimed in claim 1, wherein the feed stream has a molar ratio of ammonia to ethylene oxide of 1.3:1.

12. A process as claimed in claim 3, wherein the ammonia proportion in the bottom product of the reactive distillation column is at most 5% by weight based on the total weight of the bottom product.

13. A process as claimed in claim 3, wherein the ammonia proportion in the bottom product of the reactive distillation column is at most 2% by weight based on the total weight of the bottom product.

14. A process as claimed in claim 1, wherein the reactive distillation column is operated at a column pressure of from 30 to 50 bar absolute.

15. A process as claimed in claim 1, wherein, from the distillation column to separate ammonia and water on the one hand, monoethanolamine, diethanolamine and triethanolamine on the other hand, the ammonia- and water-containing head product is returned in its entirety via a condenser, on the head of the reactive distillation column, to the head region thereof.

* * * * *